US012672931B2

(12) United States Patent
Margiott et al.

(10) Patent No.: US 12,672,931 B2
(45) Date of Patent: *Jul. 7, 2026

(54) LAPAROSCOPIC OXIMETER AND PROTECTIVE METHOD FOR REUSE OF PORTIONS OF THE LAPAROSCOPIC OXIMETER

(71) Applicant: ViOptix, Inc., Newark, CA (US)

(72) Inventors: Alex Michael Margiott, Dunbarton, NH (US); Sean Gossin, Media, PA (US); Timothy Lee Sauder, San Francisco, CA (US); Kevin Dunk, Casto Valley, CA (US); Scott E. Coleridge, New York, NY (US); Mark Lonsinger, San Jose, CA (US)

(73) Assignee: ViOptix, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/012,792

(22) Filed: Jan. 7, 2025

(65) Prior Publication Data

US 2025/0318895 A1       Oct. 16, 2025

Related U.S. Application Data

(60) Provisional application No. 63/618,864, filed on Jan. 8, 2024.

(51) Int. Cl.
*A61B 50/30*       (2016.01)
*A61B 50/00*       (2016.01)

(52) U.S. Cl.
CPC ........ *A61B 50/30* (2016.02); *A61B 2050/002* (2016.02); *A61B 2050/3015* (2016.02); *A61B 2050/314* (2016.02)

(58) Field of Classification Search
CPC ............ A61B 50/30; A61B 2050/3015; A61B 2050/002; A61B 2050/005; A61B 2050/0051; A61B 2050/0052; A61B 2050/0053; A61B 2050/0054; A61B 2050/0055; A61B 2050/0056; A61B 2050/0057; A61B 2050/0065; A61B 2050/0066; A61B 2050/314
USPC .......................................................... 606/1
See application file for complete search history.

(56) References Cited

U.S. PATENT DOCUMENTS

| | | | | |
|---|---|---|---|---|
| 5,758,663 A | * | 6/1998 | Wilk | ........................ A61B 1/05 606/1 |
| 2019/0015625 A1 | * | 1/2019 | Neethling | .............. A61B 50/33 |

* cited by examiner

*Primary Examiner* — Aaron F Roane
(74) *Attorney, Agent, or Firm* — Aka Chan LLP

(57) ABSTRACT

A method for housing a reusable portion of an oximeter device in a sheath includes providing the oximeter device as a probe unit and a laparoscopic tube separated from each other. The probe unit is handled by a first operator in a nonsterile environment and the laparoscopic tube is handled by a second operator in a sterile environment. The first operator connects the probe unit and the laparoscopic tube to form the oximeter device. The sheath is coupled to the laparoscopic tube in a folded configuration and is pulled by the second operator to enclose the probe unit. The oximeter device is in the sterile environment when the probe unit is in the sheath. The oximeter device is for use in an intraoperative procedure and the sheath inhibits the probe unit from contacting contaminants so that the probe unit is reusable, whereas the laparoscopic tube can be disposed of.

21 Claims, 4 Drawing Sheets

LAPAROSCOPIC OXIMETER AND PROTECTIVE METHOD FOR REUSE OF PORTIONS OF THE LAPAROSCOPIC OXIMETER

CROSS-REFERENCE TO RELATED APPLICATIONS

This application claims the benefit of U.S. patent application 63/618,864, filed Jan. 8, 2024, which is incorporated by reference along with all other references cited in this application.

BACKGROUND OF THE INVENTION

The invention generally relates to optical systems that monitor oxygen levels in tissue. More specifically, the invention relates to a protective sheath that houses a reusable portion of the laparoscopic oximeter and inhibits contaminants from contacting the reusable portion of the oximeter.

Oximeters are medical devices used to measure the oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or personal training for a marathon); and veterinary purposes (e.g., animal monitoring).

Pulse oximeters and tissue oximeters are two types of oximeters that operate on different principles. A pulse oximeter uses a patient's pulse to make measurements. A pulse oximeter typically measures the absorbance of light due to pulsing arterial blood. In contrast, a tissue oximeter does not need a pulse in order to function and can be used to make oxygen saturation measurements of a tissue flap that has been disconnected from a blood supply or of tissue, such as internal organs that are connected to a blood supply.

Human tissue, as an example, includes a variety of light-absorbing molecules referred to as chromophores. Such chromophores include oxygenated hemoglobin, deoxygenated hemoglobin, melanin, water, lipid, and cytochrome. Oxygenated hemoglobin, deoxygenated hemoglobin, and melanin are the most dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, designing oximeters for reuse or designing a portion of an oximeter for reuse; improving form factor; improving measurement accuracy; reducing measurement time; lowering cost; reducing size, weight, or form factor, such as for portability; reducing power consumption; and for other reasons, and any combination of these measurements.

Therefore, there is a need for improved tissue oximeter devices and methods for reusing these probes.

BRIEF SUMMARY OF THE INVENTION

A laparoscopic medical device includes an oximeter sensor at its tip, which allows for oxygen saturation measurements to be made laparoscopically. The laparoscopic medical device includes a probe unit and a laparoscopic tube that detachably connects with the probe unit so that the laparoscopic tube can be replaced for different patient surgeries and the probe unit can be reused. Replaceable laparoscopic tubes facilitate efficient sterility for patient surgeries, and a reusable probe unit facilitates cost savings and ecological conservation for a probe unit that includes costly circuitry.

In the separable design, a sheath is connected to the laparoscopic tube. The sheath and laparoscopic tube are provided in a sterile package that is opened by a sterile operator located in a sterile environment, such as an operating room. The probe unit is provided in a sanitary package or sterile package that is opened by a nonsterile operator located in a nonsterile environment. The sterile operator removes the laparoscopic tube and sheath from the sterile package in the sterile environment, and the nonsterile operator removes the probe unit from the sanitary package in the nonsterile environment. The nonsterile operator, or the operators working together, connects the laparoscopic tube and the probe unit, such as by a push and twist connector, to form an oximeter device for laparoscopic use.

Thereafter, the nonsterile operator releases their hold on the probe unit, and the sterile operator extends the sheath to house the probe unit inside the sheath. The sheath is sealed so that the probe unit is located in the sealed and sterile environment inside the sheath. When the probe unit is in the sheath, the oximeter device and sheath become part of the sterile environment for use in an intraoperative procedure. The method of using the sheath and initially separated probe unit and laparoscopic tube allows for reuse of the probe unit and disposal of the laparoscopic tube after use. Reuse of the probe unit saves cost by avoiding using a new probe unit for each surgery and provides ecological conservation.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
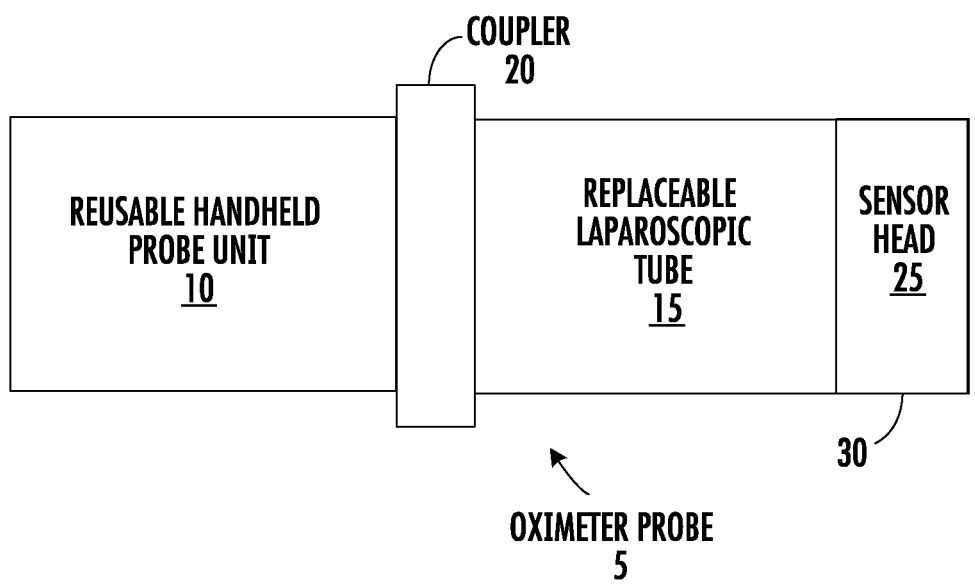
FIG. 1 shows an image of an oximeter device, in an implementation.

FIG. 1 shows an image of an oximeter device 5 in an implementation. Oximeter device 5 is configured to make tissue oximetry measurements of tissue, such as internal tissue, intraoperatively. Oximeter device 5 may be a handheld device that includes a probe unit 10 and a laparoscopic tube 15 extending from the probe unit. Laparoscopic tube 15 includes a tip 30 and a sensor head 30 located at the tip. The probe unit is coupled to the laparoscopic tube by a coupler 20. Tip 30 is distally located with respect to coupler 20. Coupler 20 allows the probe unit 10 and laparoscopic tube 15 to be coupled and decoupled so that a laparoscopic tube can be replaced by a new laparoscopic tube after use and so that the probe unit can be reused.

The probe unit includes a number of elements that are relatively costly. Configuring the oximeter device for reuse of the probe unit allows for cost saving and ecological conservation. Cost savings are facilitated by not having to replace the probe unit for each surgery that the probe unit is used for, and ecological conservation is facilitated by delaying disposal of the probe unit until after it has been used a number of times. Further, many elements of the probe unit may be recyclable after repeated use, such as circuits and other elements, which further facilitates ecological conservation.

The oximeter device is fully self-contained and does not need to be connected to another device to be fully operational, in an implementation. That is, the oximeter device does not need to be wire connected or wirelessly connected to another device to be fully operational for taking oximetry measurements and displaying the measurements. In an implementation, the oximeter device can connect to other devices, such as one or more other medical devices, a computer system, a display, any of these devices or systems in any combination, or other devices or systems. The connections can be wired or wireless connections.

In an implementation, the laparoscopic tube of the oximeter device is adapted for intraoperative use in a patient and can be introduced into the abdominal cavity of the patient through a trocar. An outer surface of the laparoscopic tube can be smooth so that the laparoscopic tube can slide through the trocar smoothly, can rotate within the trocar smoothly, and can slide into contact and past patient tissue smoothly and without abrading the tissue. The oximeter device can be used on various internal tissues to determine various oximetry information for the tissues. The tissue under test can include intestinal tissue, such as the large intestine, small intestine, and tissue that supports these tissues, such as the mesentery tissue, muscle, the liver, kidneys, or other internal tissue.

Figure 2:
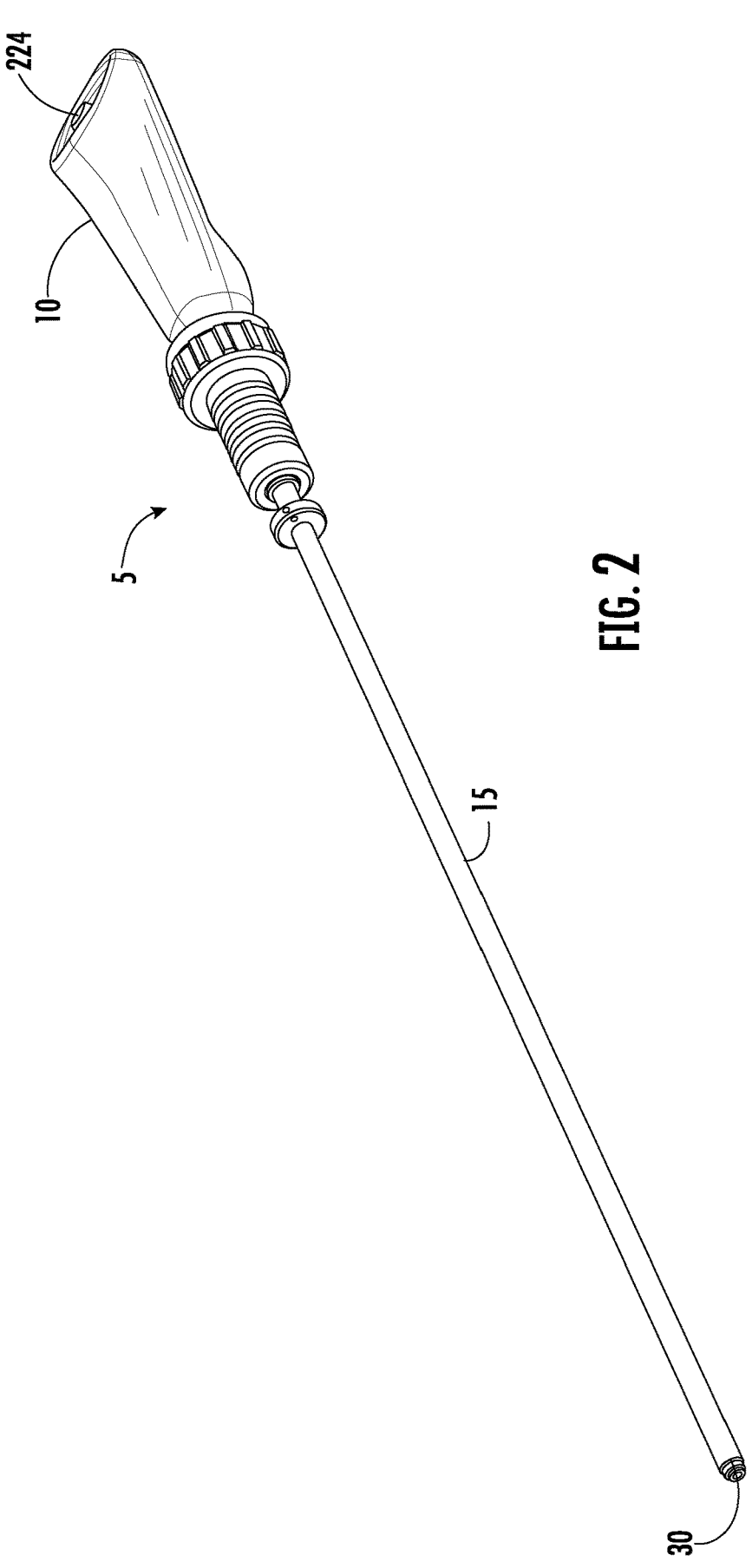
FIG. 2 shows an image of an oximeter device, in an implementation.

FIG. 2 shows oximeter device 5, in an implementation. Oximeter device 5 includes probe unit 10 connected to laparoscopic tube 15. The laparoscopic tube 15 can be detachable from the probe unit so that the tube can be replaced after a surgery. The probe unit can include a display 224 that displays operational information for use and oximetry information when tissue measurements are made. The laparoscopic tube includes a tip 30 that houses a sensor head, which emits light (e.g., visible light, infrared light, or both) into tissue and collects reflected light that is reflected from the irradiated tissue. The sensor head is sometimes referred to as a probe tip. In an implementation, the laparoscopic tube is a passive device that includes optical fibers, but does not include light generating and emitting devices, such as one or more LEDs and does not include photodetectors. In another implementation, the laparoscopic tube includes the described optical fibers and photodetectors, but does not include light generating and emitting devices. In another implementation, the laparoscopic tube includes the described optical fibers, light generating and emitting devices, and photodetectors. In an implementation where the LEDs and photodetectors are located in the probe unit and the laparoscopic tube is a passive device that includes the optical fibers, the LEDs and photodetectors are sometimes referred to as the sensor head. The probe unit uses the reflected light to determine oximetry information, such as oxygen saturation, for the tissue. The oximetry information can thereafter be displayed on the display or on a remote display that the oximeter device can communicate with.

Figure 3:
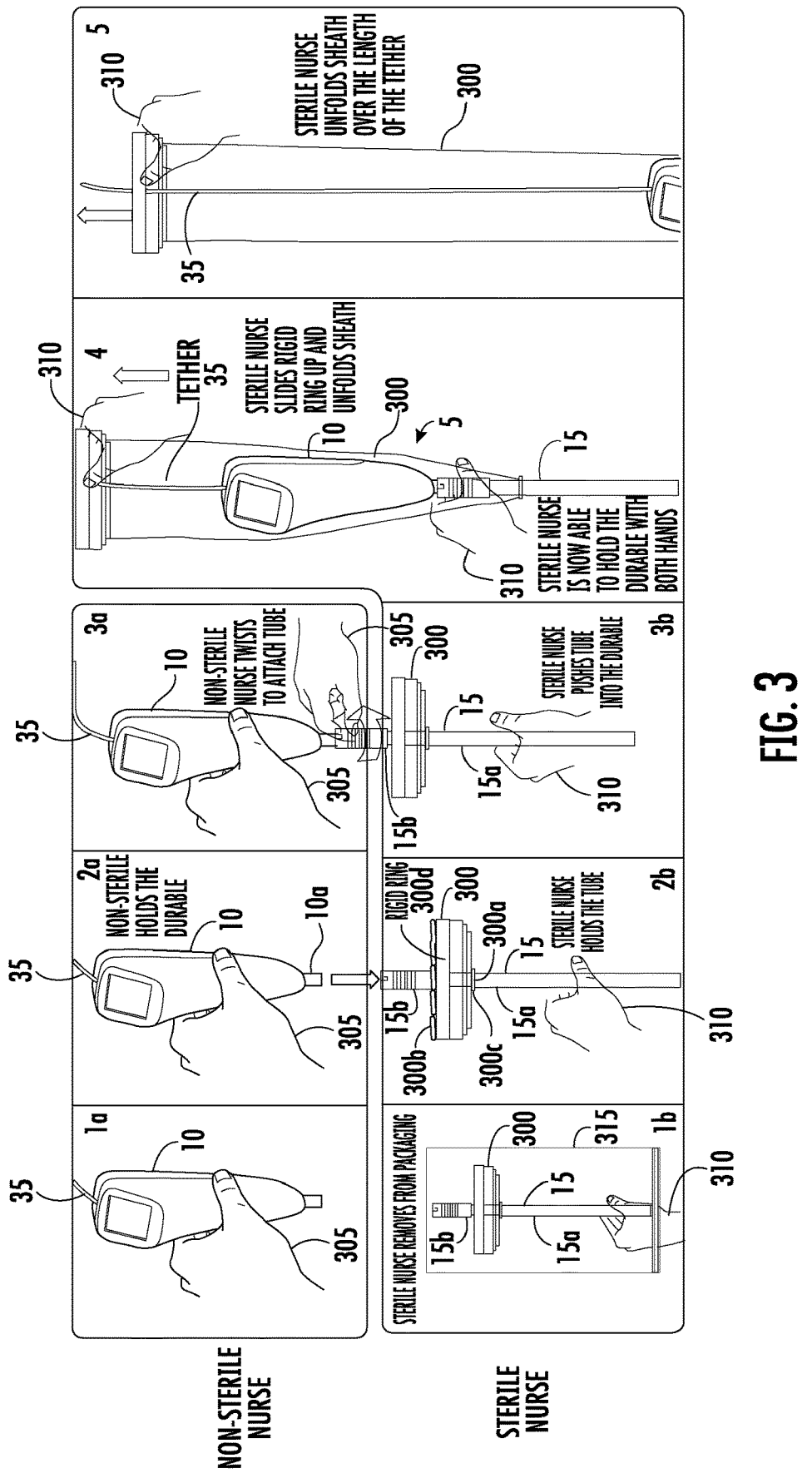
FIG. 3 shows a diagram for a method of use of the oximeter device and a sheath for the device, in an implementation.

FIG. 3 shows a diagram for a method of use of oximeter device 5 and a sheath 300, in an implementation. The method allows for a portion of the oximeter device to be placed into the sheath 300, which keeps the probe unit of the oximeter device sterile during use. Steps may be added, combined, or removed from the diagram without deviating from the scope and purview of the method.

The sheath inhibits or prevents contaminants from contacting the probe unit during use, such as when the oximeter device is used for patient surgery. The sheath can inhibit or prevent patient contaminants and other debris from contacting the probe unit. For example, the sheath can inhibit or prevent body fluids (e.g., blood), tissue (e.g., skin, muscle, fat, and other tissue), bacteria, viruses, prions, dirt, and other debris from contacting the probe unit during use. The sheath also inhibits or prevents contaminants that are on the probe unit from reaching a patient.

The physical barrier of the probe unit provided by the sheath facilitates the reuse of the probe unit. For example, the probe unit can be reused after the probe unit is sanitized. In contrast to the probe unit, the laparoscopic tube can be disposed of after use and a new laparoscopic tube can be fitted to the probe unit for reuse of the unit. The probe unit includes various circuits and other devices where reuse of the probe unit provides for cost saving and ecological conservation because the probe unit can be used multiple times prior to being disposed of.

Boxes 1a and 1b of the flow diagram of FIG. 3 show hands 305 and 310 of two different operators working together to place probe unit 10 into sheath 300. The two operators can be nurses or other medical staff. The first operator (also referred to with reference number 305) is a nonsterile operator that is in a nonsterile environment. The second operator (also referred to with reference number 310) is a sterile operator operating in a sterile environment. The boxes labeled 1a-3a in FIG. 3 represent the nonsterile environment, and boxes 1b-3b and 4-5 represent the sterile environment.

The sterile environment can be in an operating room where a surgical procedure is taking place or is going to take place using the oximeter device. The nonsterile environment can be a space inside the operating room that is separate from the sterile environment inside the operating room. A nonsterile operator in the nonsterile environment can transfer an oximeter device from the nonsterile environment into the sterile environment. For example, the nonsterile operator can place the oximeter device onto a sterile table or hand a sterile device to a sterile operator. A nonsterile environment is sometimes referred to as a nonsterile field and a sterile environment is sometimes referred to as a sterile field.

In another implementation, the nonsterile environment can be physically separated from the sterile environment by a physical barrier where a reach-through area is located between the two environments through the barrier. The nonsterile environment can be a first room and the sterile environment can be a second room where the first and second rooms are separated by the physical barrier that includes the reach-through area. The nonsterile environment and sterile environment can be in the same room where a physical barrier separates the two environments and includes a reach-through area.

The physical barrier can be a window, a door, one or more curtains, or another type of barrier. The reach-through area can be an open area created when a window separating the nonsterile and sterile areas is opened and can be closed when the window is closed. The reach-through area can be an open area created when a door separating the nonsterile and sterile areas is opened and can be closed when the door is closed. The reach-through area can be an opening in a curtain or an area where two curtains meet and can be opened by pushing one or both of the curtains to form the opening.

Referring again to FIG. 3, at an initial step in box 1*a*, in the nonsterile environment, the first operator 305 removes a probe unit 10 from the provided packaging. At the initial step in box 1*b*, the sterile operator removes a laparoscopic tube 15 from packaging 315. Packaging 315 keeps the laparoscopic tube sterile prior to use. The sterile operator may receive the laparoscopic tube in packaging 315 from the nonsterile operator, who places packaging 315 into the sterile operator's hands or onto a sterile work surface from another package that is sterile on the inside but nonsterile on the outside.

In an implementation, the laparoscopic tube includes a first portion 15*a* and a second portion 15*b*. The first portion 15*a* is an extended tube adapted to be inserted into the body cavity of a patient. The first portion can be inserted into the body cavity of a patient through a trocar. The outside surface of the extended tube can be smooth and seamless so that the extended tube can move smoothly inside a trocar and slip by tissue and internal organs without abrading the tissue and organs.

The second portion 15*b* includes a coupler that connects the laparoscopic tube to the probe unit. The coupler includes a mechanical coupler, an optical coupler, an electrical coupler, a radio frequency communication device (e.g., a near field communication (NFC) tag), or any one or more of these couplers in any combination, in an implementation. In one specific implementation, the coupler of the laparoscopic tube connects to the probe unit via a push-and-twist mechanism and method.

The NFC tag can couple to a radio frequency communication tag reader (e.g., an NFC tag reader through a radio frequency magnetic field), which is included in the probe unit. The NFC tag can form a portion of the mechanical coupler of the second portion 15*b* of the laparoscopic tube. The NFC tag reader can form a portion of a mechanical coupler of the probe unit, where the mechanical coupler of the probe unit removably couples to the mechanical coupler of the laparoscopic tube.

The NFC tag can store a variety of information that can be transferred to the probe unit by the NFC tag reader reading the information. The information can include calibration information for the laparoscopic tube, an encrypted identifier that identifies the laparoscopic tube as an authentic laparoscopic tube, an expiration date, or any combination of this information. The calibration information can also be encrypted in the NFC tag. The processor or other circuit of the probe unit can decrypt the information for use, such as not operating with a laparoscopic tube that does not provide a valid identifier or operating with a laparoscopic tube that does provide a valid identifier.

In an implementation, the NFC tag reader writes information to the NFC tag. For example, the NFC tag reader can write use information to the NFC tag that indicates that the laparoscopic tube has been used. The use information written to the NFC tag by the NFC tag reader can be encrypted information. The use information regarding the prior use of the laparoscopic tube can be used by the probe unit when the use information is read from the NCF tag later so that the probe unit does not operate with the laparoscopic tube that has been previously used or used with a laparoscopic tube that has not been previously used. The refusal by the probe unit to operate with a laparoscopic tube that has previously been used helps to ensure that the probe unit properly operates with a sterile laparoscopic tube that has not previously been used for a patient surgery and does not operate with a potentially nonsterile laparoscopic tube that has been previously used.

In an implementation, sheath 300 is connected to the laparoscopic tube. The sheath can be connected to the first portion 15*a* of the laparoscopic tube, the second portion 15*b* of the laparoscopic tube, or both. As shown in the implementation of FIG. 3, sheath 300 is connected to the first portion 15*a* of the laparoscopic tube. The sheath can be connected to the laparoscopic tube so that the sheath is held in place on the first portion 15*a*.

The laparoscopic tube is connected to the sheath at a first aperture 300*a* of the sheath. In an implementation, a retaining ring 300*c* holds the sheath in place on the first portion 15*a*. The retaining ring can be a clamp, a rubber-type O-ring, or another type of device to hold the sheath to first portion 15*a* of the laparoscopic tube. In an implementation, the first portion 15*a* includes a groove formed in the exterior surface and the retaining ring is placed over or at least partially in the groove. Other devices can connect the sheath to the first portion 15*a* of the laparoscopic tube, such as an adhesive material. The adhesive material can be glue, epoxy, tape, or another adhesive.

The sheath includes a second aperture 300*b*. The first and second apertures are at opposite ends of the sheath. The sheath may have a generally frustum shape with the first aperture at a first end of the frustum and the second aperture at a second end of the frustum. In an implementation, the frustum shape of the sheath is a frustum cone shape. In an implementation, the first and second apertures of the frustum are in parallel planes. In another implementation, the first and second apertures of the frustum are not in parallel planes. The probe unit 10 fits through the second aperture of the sheath so that the probe unit can be positioned inside the sheath. Fitting the probe unit through the second aperture is described below.

The first aperture 300*a* has a first average length across the first aperture and the second aperture has a second average length across this aperture. The second average length is about 3-20 times longer than the first average length.

In an implementation, the first aperture has a diameter that is greater than the diameter of first portion 15*a*. The diameter of the aperture of the sheath can be 0.25 millimeters to 10 millimeters greater than the diameter of the first portion 15*a*. The second aperture has a diameter that is less than the diameter of the first aperture.

At step 1*b*, the sterile operator 310 places their hand (e.g., a gloved hand) into packaging 315 to remove the laparoscopic tube from the packaging while the packaging and the laparoscopic tube are in the sterile environment. Alternatively, the sterile operator can dump the laparoscopic tube onto a sterile surface rather than removing the laparoscopic tube from the packing by placing their hand into the package to remove the laparoscopic tube using their hand.

At step 2*a*, the nonsterile operator 305 holds the probe unit and moves the probe unit and the probe unit's coupler 10*a* towards connector 15*b* of the laparoscopic tube. Coupler 10*a* can include a mechanical coupler, an optical coupler, an electrical coupler, an NFC tag reader (described above), or any combination of these devices. Coupler 10*a* is configured to couple to coupler 15*b* of the laparoscopic tube. The mechanical couplers of couplers 10*a* and 15*b* can be configured to mechanically couple, by pressing the couplers together, by pressing and twisting, or by other mechanical mechanisms (e.g., pins and apertures where the pins of one element are configured to be held in the apertures of the other element). Couplers 10*a* and 15*b* can include optical couplers that couple waveguides, such as optical fibers. Couplers 10*a* and 15*b* can include electrical couplers that electrical wires (e.g., ribbon cables) of the probe unit and laparoscopic tube. Couplers 10*a* and 15*b* can respectively include the NCF tag reader and the NFC tag.

At steps 3*a* and 3*b*, the nonsterile operator pushes couplers 10*a* and 15*b* together and releasably connects the couplers, thereby connecting the probe unit and laparoscopic tube to form the oximeter device. The connection may be accomplished by pressing the couplers together and by twist-locking coupler 15*b* to coupler 10*a*. Alternatively, both the nonsterile and sterile operators can push the coupler together and one or both of the operators can perform the twist locking of the couplers. Further, the sterile operator may keep their hand on the laparoscopic tube even though the sterile operator may not connect the probe unit and laparoscopic tube by locking the couplers together.

In an implementation, sheath 300 includes a ring 300*d*. The ring may be a rigid ring or a non-rigid ring. At step 4 the sterile operator grasps ring 300*d* and pulls the ring up towards the probe unit to expand the sheath and enclose the probe unit in the sheath. Ring 300*d* remains sterile because the nonsterile operator does not touch the ring.

The nonsterile operator can release their hold on the assembled oximeter device prior to the ring 300*d* being pulled up to enclose the oximeter device in the sheath. The sterile operator can hold the assembled oximeter device from the laparoscopic tube and the outside of the sheath and these devices will remain sterile. The oximeter device enclosed in the sheath becomes part of the sterile environment.

In an implementation, a tether 35 is attached to the top of the oximeter device. At step 5, the sterile operator can continue to hold ring 300*d* up so that the probe unit and the tether are enclosed in the sheath. The tether can be used by an operator to pull the oximeter device out of the sheath so that contaminants on the outer surface of the sheath do not contact the oximeter device after the oximeter device is used for surgery. In an implementation, a tether is not attached to the oximeter device.

This detailed description describes examples of implementations with specific measurements, angles, values, dimensions, shapes, and orientations. These examples implementations are not intended to be exhaustive or to limit the invention to the precise form described.

The measurements, for example, in millimeters or centimeters are approximate values. The values can vary due to, for example, measurement or manufacturing tolerances (as will be understood by those of ordinary skill in the art) or other factors (as will be further understood by those of ordinary skill in the art). A measurement can vary, for example, by plus or minus 1 percent, plus or minus 5 percent, plus or minus 10 percent, plus or minus 15 percent, plus or minus 20 percent, plus or minus 1 to 5 percent, plus or minus 5 to 10 percent, or plus or minus 15 to 20 percent. Further, the measurements are for a specific implementation of the device, and other implementations can have different values, such as certain measurements, dimensions, or both made longer to accommodate smaller hands or larger hands or to access tissue in a particular location of a patient's body.

For the specific implementations described, some specific values, ranges of values, and numbers are provided. These values indicate, for example, dimension, angles, ranges, frequencies, wavelengths, numbers, a relationship (e.g., relative value), and other quantities (e.g., numbers of sensors, sources, detectors, diodes, fiber optic cables, and so forth). Some measurements are for a specific implementation of the device, and other implementations can have different values, such as certain dimensions made larger for a larger-sized product, or smaller for a smaller-sized product. The device may be made proportionally larger or smaller by adjusting relative measurements proportionally (e.g., maintaining the same or about the same ratio between different measurements). In various implementations, the values (or numbers or quantities) can be the same as the value given, about the same of the value given, at least or greater than the value given, or can be at most or less than the value given, or any combination of these. The values (or numbers or quantities) can also be within a range of any two values given or a range including the two values given. When a range is given, the range can also include any number within that range to any other number within that range.

The dimensions, for example, along an axis, a rotational orientation, or both are approximate values. The dimensions can be in values, directions, angles, or any combination of these dimension. Dimensions, for example, of values in millimeters or centimeters, of directions along an axis or at an angular orientation relative to an axis, of an angular orientation are approximate values. The values, direction, and angles can vary due to, for example, measurement or manufacturing tolerances or other factors. A dimension can vary, for example, by plus or minus 0.1 percent, plus or minus 0.2 percent, plus or minus 0.5 percent, plus or minus 1 percent, plus or minus 5 percent, plus or minus 10 percent, plus or minus 15 percent, plus or minus 20 percent, plus or minus 0.1 to 0.2 percent, plus or minus 0.2 to 0.5 percent, plus or minus 0.5 to 1 percent, plus or minus 1 to 5 percent, plus or minus 5 to 10 percent, plus or minus 10 to 15 percent, or plus or minus 15 to 20 percent.

The shapes, for example, a geometric shape can be approximate shapes. The shapes can be in values, directions, angles, terms, or any combination of these shapes. The shapes can vary due to, for example, measurement or manufacturing tolerances or other factors. A shape can vary, for example, by plus or minus 0.1 percent, plus or minus 0.2 percent, plus or minus 0.5 percent, plus or minus 1 percent, plus or minus 5 percent, plus or minus 10 percent, plus or minus 15 percent, plus or minus 20 percent, plus or minus 0.1 to 0.2 percent, plus or minus 0.2 to 0.5 percent, plus or minus 0.5 to 1 percent, plus or minus 1 to 5 percent, plus or minus 5 to 10 percent, plus or minus 10 to 15 percent, or plus or minus 15 to 20 percent.

The orientations, for example, parallel, perpendicular, transverse, and angle are approximate values. The orientation can be in values, directions, angles, terms, or any combination of these orientations. Orientations, for example, of terms or angles can be approximate orientations. The orientations vary due to, for example, measurement or manufacturing tolerances or other factors. An orientation can vary, for example, by plus or minus 0.1 percent, plus or minus 0.2 percent, plus or minus 0.5 percent, plus or minus 1 percent, plus or minus 5 percent, plus or minus 10 percent, plus or minus 15 percent, or plus or minus 20 percent. Terms, such as about, substantially, approximately, or other relative terms can include the described ranges as will be readily understood by those of ordinary skill in the art and can include ranges that will be understood by those of ordinary skill in the art.

Figure 4:
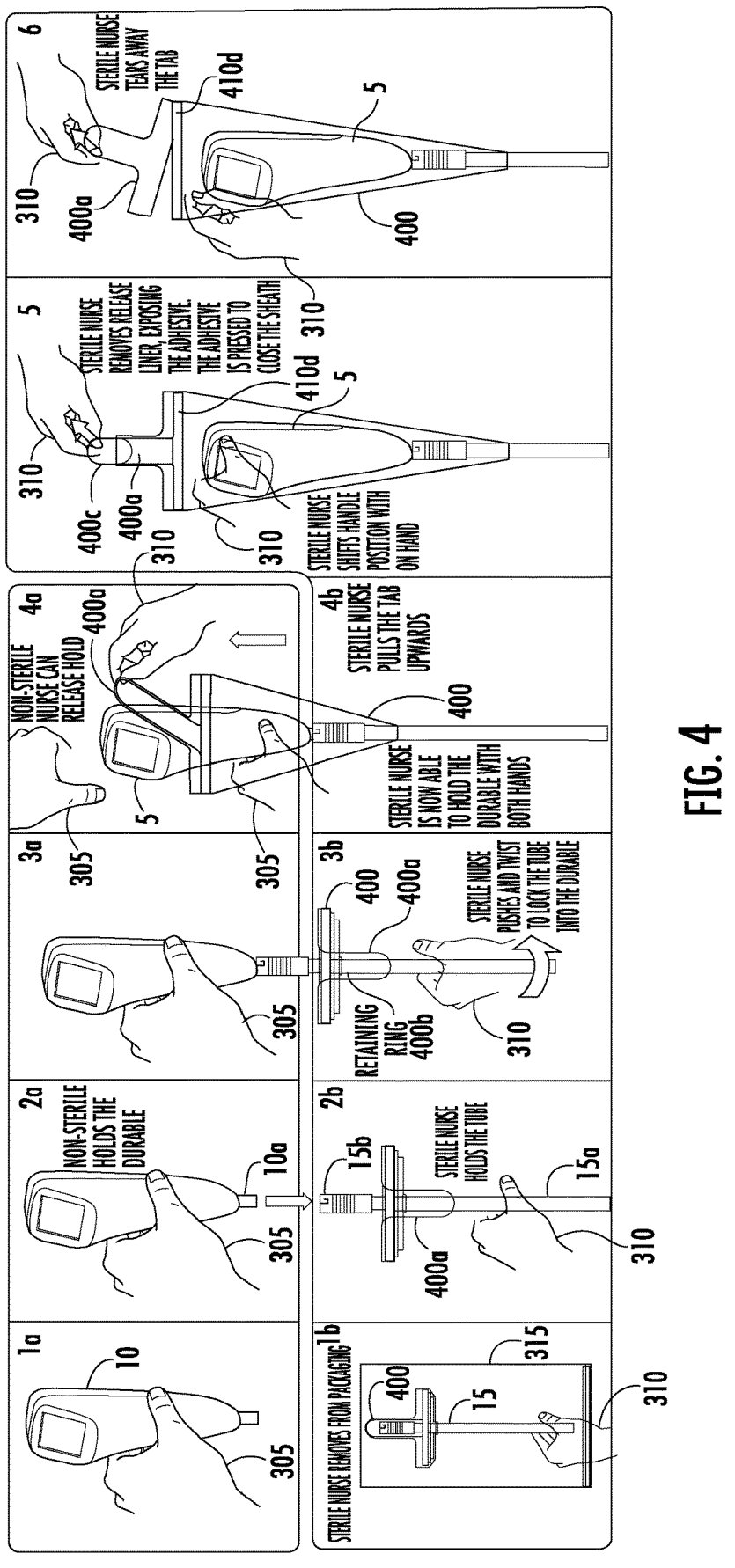
FIG. 4 shows a diagram for a method of use of the oximeter device and a sheath for the device, in an implementation.

FIG. 4 shows a diagram for a method of use of oximeter device 5 and a sheath 400, in an implementation. The method allows for a portion of the oximeter device to be placed into the sheath 400, which keeps the probe unit of the oximeter device sterile during use. Steps may be added, combined, or removed from the diagram without deviating from the scope and purview of the method.

Boxes 1*a* and 1*b* of the flow diagram of FIG. 3 show hands 305 and 310 of two different operators working together to place probe unit 10 into sheath 400. The two operators can be nurses or other medical staff. The first operator (also referred to with reference number 305) is in a nonsterile environment and the second operator (also referred to with reference number 310) is in a sterile environment. The boxes labeled 1*a*-4*a* in FIG. 3 represent the nonsterile environment, and boxes 1*b*-4*b* and 5-6 represent the sterile environment.

At an initial step in box 1*a* in the nonsterile environment, the first operator 305 removes a probe unit 10 from the provided packaging. At the initial step in box 1*b*, the sterile operator removes a laparoscopic tube 15 from packaging 315. Packaging 315 keeps the laparoscopic tube sterile prior to use.

The laparoscopic tube includes a first portion 15*a* and a second portion 15*b*. The first portion 15*a* is an extended tube adapted to be inserted into the body cavity of a patient. The first portion can be inserted into the body cavity of a patient through a trocar. The outside surface of the extended tube can be smooth and seamless so that the extended tube can move smoothly inside a trocar and slip by tissue and internal organs without abrading the tissue and organs.

The second portion 15*b* includes one or more couplers that connect the laparoscopic tube to the probe unit. The coupler includes a mechanical coupler. The mechanical coupler can include an optical coupler, an electrical coupler, and an NFC tag, or anyone or more of these couplers in any combination. The coupler can connect to the probe unit via a push-and-twist mechanism and method. The NFC tag can couple to an NFC tag reader (e.g., through a radio frequency magnetic field), which is included in the probe unit. The NFC tag and NFC tag reader can couple when the laparoscopic tube is coupled to the probe unit and the reader is powered for reading the tag. The NFC tag can form a portion of the mechanical coupler of the second portion 15*b* of the laparoscopic tube. The NFC tag reader can form a portion of a mechanical coupler of the probe unit, where the mechanical coupler of the probe unit removably couples to the mechanical coupler of the laparoscopic tube. In an implementation, sheath 400 is connected to the laparoscopic tube. The sheath can be connected to the first portion 15*a* of the laparoscopic tube, the second portion 15*b* of the laparoscopic tube, or both. As shown in the implementation of FIG. 3, sheath 400 is connected to the first portion 15*a* of the laparoscopic tube.

The sheath includes a first aperture that the first portion 15*b* of the laparoscopic tube fits through. The first aperture can be circular or noncircular. In an implementation where the aperture is circular, the diameter of the aperture of the sheath can be 0.25 millimeters to 10 millimeters greater than the diameter of the first portion 15*a*. The aperture has a diameter that is greater than the diameter of first portion 15*a*. The diameter of the aperture of the sheath can be 0.25 millimeters to 10 millimeters greater than the diameter of the first portion 15*a*.

The sheath can be connected to the laparoscopic tube so that the sheath is held in place on the first portion 15*a*. In an implementation, a retaining ring 400*b* holds the sheath in place on the first portion 15*a*. The retaining ring can be a clamp, a rubber-type o-ring, or another type of device to hold the sheath to first portion 15*a* of the laparoscopic tube.

In an implementation, the first portion 15*a* includes a groove formed in the exterior surface and the retaining ring is placed over or at least partially in the groove. Other devices can connect the sheath to the first portion 15*a* of the laparoscopic tube, such as an adhesive.

At step 1*b*, the sterile operator 310 places their hand (e.g., a gloved hand) into packaging 315 to remove the laparoscopic tube from the packaging while the packaging and the laparoscopic tube are in the sterile environment. After removing the laparoscopic tube from the packaging, a pull tab 400*a* of the sheath is exposed, in one implementation. In an alternative implementation, the sheath does not include a pull tab. In one configuration of the sheath inside the packaging, the pull tab is registered with connector 15*b* of the laparoscopic tube as shown in box 1*b*. In another configuration of the sheath inside the packaging, the pull tab is registered with the first portion 15*a* of the laparoscopic tube. Box 2*b* shows the pull tab registered with the laparoscopic tube.

At step 2*a*, the nonsterile operator 305 holds the probe unit and moves the probe unit and the unit's coupler 10*a* towards connector 15*b* of the laparoscopic tube. Coupler 10*a* can include a mechanical coupler, an optical coupler, an electrical coupler, or any combination of these couplers. Coupler 10*a* is configured to couple to coupler 15*b* of the laparoscopic tube. The mechanical couplers of couplers 10*a* and 15*b* can be configured to mechanically couple, just as by pressing the coupler together and twisting or by other mechanical mechanisms (e.g., pins and apertures where the pins of one element are configured to be held in the apertures of the other element). The optical coupler of couplers 10*a* and 15*b* can include a coupler that couples waveguides, such as optical fibers. The electrical couplers of couplers 10*a* and 15*b* can be couplers that couple electrical conductors, such as wires (e.g., in the form of ribbon cables). The NFC tag and NFC tag reader can be coupled when the mechanical couplers are coupled as described above.

At step 2*b*, the sterile operator 310 removes or has removed the laparoscopic tube from packaging 315. Thereafter, the sterile operator holds the laparoscopic tube in their hand by the first portion 15*a* of the tube. The sterile operator also moves coupler 15*b* of the laparoscopic tube towards coupler 10*a* of the probe unit. The probe unit remains in the nonsterile environment and the laparoscopic tube remains in the sterile environment.

In one implementation, at steps 3*a* and 3*b*, the nonsterile operator pushes couplers 10*a* and 15*b* together and releasably locks the probe unit and laparoscopic tube together. Locking may be accomplished by pressing the couplers together (e.g., pins entering apertures), by twist locking, or by other devices and methods. In an alternative implementation, one or both of the nonsterile and sterile operators can perform the steps for releasably locking the probe unit and the laparoscopic tube to form the oximeter device.

At steps 4*a* and 4*b*, the sterile operator grasps tab 400*a* and pulls the tab up towards the probe unit to expand the sheath from a collapsed configuration (steps 1*a*-3*a*) so that the probe unit is placed inside the sheath. The sterile operator can thereafter hold the assembled oximeter device and the nonsterile operator can release their hold on the assembled oximeter device. In an implementation where the sheath does not include tab 400*a*, the sterile operator can pull up the sheath by the top edge of the sheath at the top opening.

At step 5, the sterile operator can continue to pull tab 400*a* up so that the probe unit of the assembled oximeter device is entirely located in the sheath. The oximeter device and sheath become part of the sterile environment when the oximeter device is inside the sheath.

The sheath includes a liner 400c that covers an adhesive film 400d, in an implementation. At step 5, the sterile operator pulls the liner free from the adhesive layer exposing the adhesive layer. The sterile operator can use both of their hands to hold the sheath and assembled oximeter device when removing the liner from the adhesive film as shown in FIG. 3. In an implementation, where the sheath does not include tab 400a, the liner can be located at the top inside edge of the sheath and can be removed by the sterile operator.

At step 6, the sterile operator removes tab 400a or a portion of the tab (such as a portion of the tab that has contacted the probe unit) from the sheath. The tab or a portion of the tab can have a perforated connection to the sheath so that the tab is removed from the sheath in a controlled manner and does not tear or otherwise damage (e.g., deform) the sheath.

When the probe unit is in the sheath and the adhesive is exposed by removing liner 400c, the probe unit is sealed in the sheath by the sterile operator by sticking the adhesive film that is located on one side of the sheath onto another side of the sheath. For example, the adhesive can be located near or at a top edge of the sheath, such as adjacent to a top opening of the sheath. A first portion of the sheath near or at the top edge of the sheath may be adhered to a second portion of the sheath near or at the top edge of the sheath. The first and second portions may be inside surfaces of the sheath. In another implementation, the portion of the sheath that the adhesive is on is folded over another portion of the sheath and is adhered to an outer surface of the sheath. After the sides of the sheath are adhered together by the adhesive, the oximeter device is sealed in the sheath and is protected from being contacted by contaminants during use of the assembled oximeter device. In another implementation, the sheath includes a press seal at the top edge of the sheath, such as the press seal of a Ziploc® bag. Ziploc® is a registered trademark of SC Johnson of Racine, Wisconsin.

Tab 400a may be removed from the sheath before or after the assembled oximeter device is sealed into the closed sheath. In an alternative implementation, the tab is left on the sheath during use. For example, the tab may also be coated with the adhesive and the tab adhered to another surface of the sheath may aid in sealing the sheath and aid in inhibiting contaminants from contacting the probe unit during use of the oximeter device. When the probe unit is sealed in the sheath, contaminants, such as viruses, bacteria, prions, fungus, dirt, and other debris are inhibited from contacting the probe unit.

The sheath is formed of a flexible material, a rubberized material, plastic or a plastic-type material, where the sheath material blocks patient tissue and fluid and other debris from contacting the portion of the oximeter device that is covered by the sheath. The sheath can also block one or more prions, viruses, bacteria, fungi, and other contaminants from contacting the portion of the oximeter device that is covered by the sheath.

The sheath can be formed of polycarbonate, latex rubber, polyurethane, polyisoprene, nitrile, silicone, polymer, plastic, cellophane, polyester film (i.e., BoPET film, sold under the trademarked brand names Mylar, Melinex, Hostaphan, and other trademarked names), polyethylene film (e.g., low density polyethylene (LDPE), linear low density polyethylene (LLDPE), medium density polyethylene (MDPE), high density polyethylene (HDPE, aka HD, or a combination of one or more of these materials that form a film), a combination of ethylene methyl acrylate copolymer and polyethylene film, nylon film, polyvinyl chloride film with or without a plasticizer, or other materials that prevents tissue, fluid, prions, viruses, bacteria, fungi or other contaminants from contacting the probe unit of the formed of the assembled oximeter device. The sheath can be a laminate of any one or more of the film materials mentioned above, such as a laminate of BoPet and polyethylene (e.g., LLDPE), another polyester layer, or another material. The sheath can be a film that is a mixture of materials that are used for making film, such as a mixture of LLDPE and HDPE.

The material forming the sheath is transparent, in an implementation. Transparency allows for a user of the formed oximeter device to see the display of the oximeter device where oximetry information is displayed for measured tissue. In another implementation, the sheath is partially transparent and still allows for the display to be viewed through the sheath.

The sheath can conform to the shape of the oximeter device. For example, the sheath can be provided flat, folded, or rolled and opened to receive the probe unit. If the sheath is provided rolled up or folded, the sheath can be unrolled or unfolded onto the probe unit to conform to the probe unit for use. Further, if one or more panels are stretchable, the sheath can be stretched when the probe unit is received in the opening of the sheath, and thereafter the one or more panels can contract to conform to the shape of the oximeter device. In an implementation, when the sheath is open and expanded, the sheath has an approximately conical shape or a frustum cone shape. The small opening of the sheath where the laparoscopic tube is located and held in place by the ring is the top of the cone or frustum cone. The larger opening of the sheath that is extended by pulling the tab is the base of the cone or frustum cone.

The sheath can be formed as a continuous material without seams or can be formed of a number of panels that are connected, such as via glue, epoxy, sonic welding, or other connection material and connection techniques. The panels can be formed of the same material or different materials. The sheath is provided in a compact configuration, such as a folded configuration as shown in steps 1b, 2b, and 3b. The sheath is unfolded from the compact configuration to an expanded configuration for use as shown in steps 4a, 4b, 5, and 6. The compact configuration (e.g., folded) of the sheath before expanding (e.g., unfolding) and use allow the sheath to maintain its intended shape after being unfolded.

In an implementation, to block viruses, the sheath is formed of a material that has pore sizes of approximately 100 nanometers or less, approximately 50 nanometers or less, approximately 20 nanometers or less; or approximately 15 nanometers or less to block the smallest known viruses. In an implementation, to block proteins, such as prions, the sheath is formed of a material that has pore sizes of approximately 5-10 nanometers or less. In an implementation, to block fluids, such as water, the sheath is formed of a material that has pore sizes of approximately 0.30-0.25 nanometers or less.

Packaging 315 is a sanitary enclosure formed of any one or more of the above described materials that preserve the sterility of the sheath prior to use, in an implementation. Packaging 315 can be a blister pack, zipper storage bag (sometimes referred to as a press seal bag), a slider storage bag, or a zipper bag that is a flexible rectangular storage bag.

This description of the invention has been presented for the purposes of illustration and description. It is not intended to be exhaustive or to limit the invention to the precise form described, and many modifications and variations are possible in light of the teaching above. Elements of the various implementations can be used with other implementations in a number of ways, such as combinations, substitutions, or both. The implementations were chosen and described in order to best explain the principles of the invention and its practical applications. This description will enable others skilled in the art to best utilize and practice the invention in various implementations and with various modifications as are suited to a particular use. The scope of the invention is defined by the following claims.

The invention claimed is:

1. A method comprising:
    forming a sheath comprising an interior wall and an exterior wall, wherein the sheath comprises a first open end and a second open end, opposite the first open end;
    adhering an adhesive layer to a first portion of the interior wall of the sheath;
    covering the adhesive layer with a removable adhesive liner;
    providing a contact area of the sheath at a second portion of the interior wall, wherein the second portion is opposite of the first portion;
    forming a tab coupled to an edge of the interior and exterior walls at the first open end;
    forming the tab to fold against the exterior wall of the sheath along a fold line so that a tab end of the tab extends in a direction toward the second open end;
    forming the tab to unfold along the fold line so that the tab end that extends from the first open end away from the second open end; and
    coupling a ring to the exterior wall nearer to the second open end than the first open end, wherein the ring comprises an elastic material to press the exterior wall in a direction towards the interior wall.

2. The method of claim 1 comprising forming perforations along the fold line.

3. The method of claim 1 comprising providing the removable adhesive liner removably covers at least a portion of the tab.

4. The method of claim 1 allowing for the placement of a portion of a laparoscopic tube inside the second open end; and
    forming the ring to seal the sheath to the laparoscopic tube at the second open end when the laparoscopic tube is inside the second open end.

5. The method of claim 1 comprising forming the adhesive layer to not be formed on the contact area.

6. The method of claim 1 comprising forming a longitudinal axis of the adhesive layer parallel to the fold line.

7. The method of claim 6 comprising forming the longitudinal axis of the adhesive layer to be transverse to an axis of the sheath that passes through the first and second open ends.

8. The method of claim 1 comprising providing after the removable adhesive liner is removed, the adhesive layer becomes exposed and can be coupled to the contact area of the sheath, whereby the sheath becomes sealed at the first open end.

9. The method of claim 1 comprising forming portions of the interior and exterior walls nearer to the first open end than the second open end to be translucent.

10. The method of claim 1 comprising forming the interior and exterior walls to be seamless.

11. The method of claim 10 comprising forming the interior and exterior walls to be smooth.

12. The method of claim 1 comprising forming the adhesive material to have a longitudinal length that is at least half of a circumference of an opening of the first open end.

13. A method comprising:
    forming a sheath comprising an interior wall and an exterior wall, wherein the sheath comprises a first open end and a second open end, opposite the first open end;
    accordion folding the interior and exterior walls of the sheath from the first open end to the second open end
    forming the interior and exterior walls to have continuous surfaces between the first and second open ends,
    adhering an adhesive layer to a first portion of the interior wall of the sheath;
    covering the adhesive layer with a removable adhesive liner;
    providing a contact area of the sheath at a second portion of the interior wall, wherein the second portion is opposite of the first portion;
    forming a tab on an edge of the interior and exterior walls at the first open end;
    forming the tab to unfold to have an unfolded configuration wherein a tab end of the tab extends from the first open end away from the second open end;
    forming the tab to fold along a fold line to have a folded configuration so that the tab is against the exterior wall of the sheath and the tab end extends past the second open end; and
    coupling a ring around the exterior wall nearer to the second open end than the first open end, wherein the ring comprises an elastic material to press the exterior wall in a direction towards the interior wall.

14. The method of claim 13 comprising providing after the tab is unfolded, the tab can be pulled to at least partially open the accordion folds.

15. The method of claim 13 comprising perforating the fold line.

16. The method of claim 13 comprising providing the adhesive layer is not coupled to the contact area when the adhesive layer is coupled to the first portion of the interior wall of the sheath.

17. The method of claim 13 comprising forming a longitudinal axis of the adhesive layer parallel to the fold line.

18. The method of claim 17 comprising forming the longitudinal axis of the adhesive layer transverse to an axis of the sheath that passes through the first and second open ends.

19. The method of claim 13 comprising allowing after the removable adhesive liner is removed, the adhesive layer becomes exposed and can be coupled to the contact area of the sheath, whereby the sheath becomes sealed at the first open end.

20. The method of claim 13 comprising forming the interior and exterior walls to comprise a translucent portion nearer to the first open end than the second open end.

21. A method comprising:
    forming a kit comprising forming a sheath according to the method claim 1;
    inserting at least a portion of a laparoscopic tube in a opening at the second open end of the sheath;
    sealing the interior wall of the sheath to the portion of the laparoscopic tube using the ring;
    inserting the laparoscopic tube and the sheath in a first package to preserve sterility of the laparoscopic tube and the sheath; and inserting a probe unit in a second package to preserve
sanitation of the probe unit.

* * * * *